United States Patent
Gohrt et al.

(10) Patent No.: US 6,951,967 B2
(45) Date of Patent: Oct. 4, 2005

(54) PROCESS FOR THE PREPARATION OF TERTIARY ALCOHOLS BY THE HYDRATION OF TERTIARY OLEFINS IN A REACTIVE RECTIFICATION USING A STRUCTURED MULTI-PURPOSE PACKING

(75) Inventors: Axel Gohrt, Cologne (DE); Joachim Grub, Dormagen (DE); Stefan Kaminsky, Dormagen (DE); Stephan Muller, Pulheim (DE); Brian Schwegler, Leverkusen (DE)

(73) Assignees: EC Erdolchemie GmbH, Cologne (DE); Bayer AG, Leverkusen (DE)

( * ) Notice: Subject to any disclaimer, the term of this patent is extended or adjusted under 35 U.S.C. 154(b) by 80 days.

(21) Appl. No.: 10/365,497

(22) Filed: Feb. 13, 2003

(65) Prior Publication Data

US 2003/0120123 A1 Jun. 26, 2003

Related U.S. Application Data

(63) Continuation of application No. 09/974,059, filed on Oct. 11, 2001, now abandoned.

(30) Foreign Application Priority Data

Oct. 12, 2000 (DE) .......................................... 100 50 627

(51) Int. Cl.$^7$ .............................................. C07C 29/04
(52) U.S. Cl. ........................ 568/895; 568/896; 568/897; 568/898; 568/899; 568/900; 568/901
(58) Field of Search ................................. 568/895, 896, 568/897, 898, 899, 900, 901

(56) References Cited

U.S. PATENT DOCUMENTS 5,417,938 A  5/1995  Shelden et al. .............. 422/196

OTHER PUBLICATIONS

Gonzalez et al., Ind. Eng. Chem. Res. 1997, vol. 36, pp. 3845–3853.

*Primary Examiner*—Elvis O. Price
(74) *Attorney, Agent, or Firm*—Finnegan, Henderson, Farabow, Garrett and Dunner, L.L.P.

(57) ABSTRACT

Tertiary alcohols can be prepared by the hydration of tertiary olefins having the same number of carbon atoms on an acidic ion exchanger using special structured multi-purpose packings for heterogeneous reactive rectification. An excellent yield and purity of the alcohol and an extended service life of the catalyst are achieved.

14 Claims, 6 Drawing Sheets

Fig. 2a:
Fig. 3a:
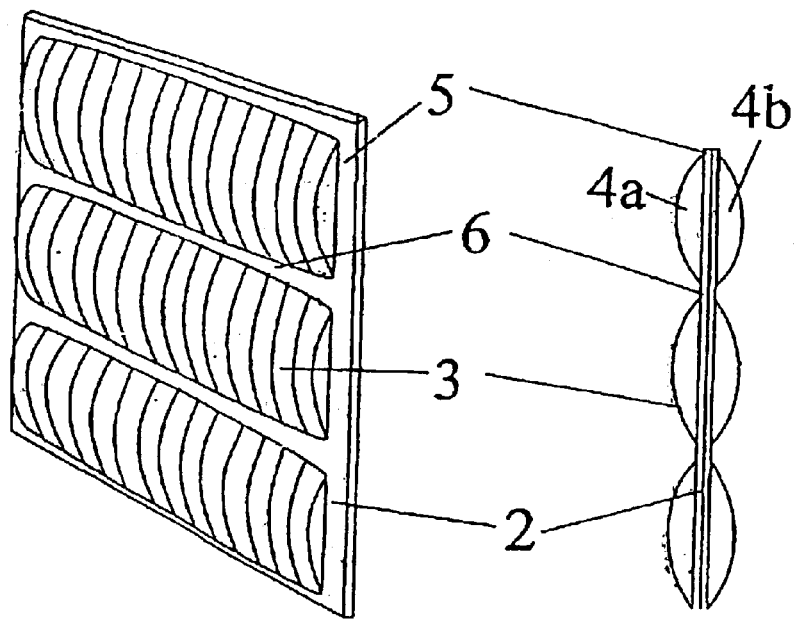
Fig. 2b:
Fig. 3b:
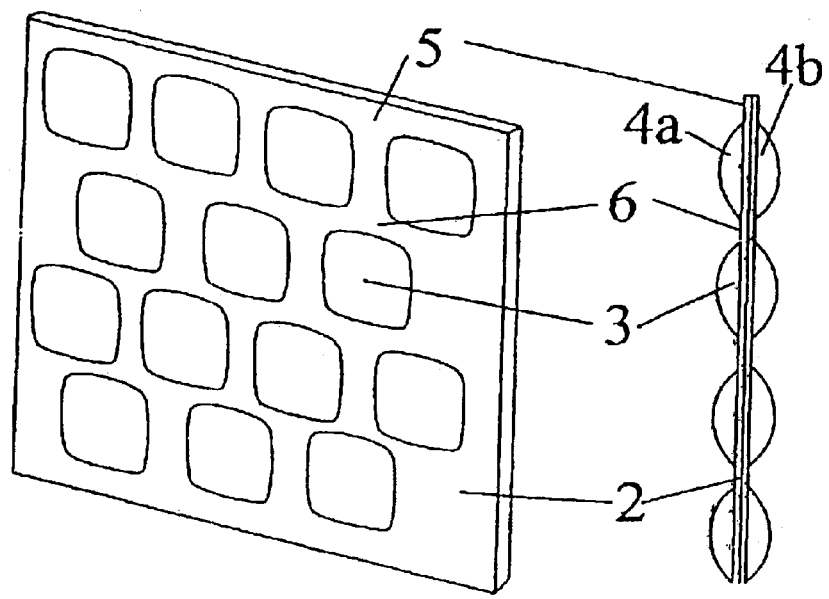

PROCESS FOR THE PREPARATION OF TERTIARY ALCOHOLS BY THE HYDRATION OF TERTIARY OLEFINS IN A REACTIVE RECTIFICATION USING A STRUCTURED MULTI-PURPOSE PACKING

This is a continuation of U.S. Ser. No. 09/974,059 filed Oct. 11, 2001, which is now abandoned.

BACKGROUND OF THE INVENTION

The present invention relates to a process for the preparation of tertiary alcohols by the hydration of tertiary olefins on an acidic ion exchanger in a reactive rectification using a structured multi-purpose packing.

From U.S. Pat. No. 2,813,908, it is already known to hydrate olefins on styrene-divinyl-benzene polymers containing sulfonic acid groups. This process is performed at temperatures of from 121 to 218° C. and pressures of up to 211 bar, but when isobutene is used, it results in an extensive formation of isobutene polymers.

Especially known from U.S. Pat. No. 3,257,469 is the preparation of tertiary amyl alcohol (TAA) on such acidic ion exchangers containing sulfonic acid groups by the reaction of isoamylene with a molar excess of water. This is effected, for example, at a pressure of 35 bar and a temperature of from 66 to 107° C. A proportion of TAA in the reaction product which is sufficient for industrial purposes is achieved by including solvents, of which isopropanol and acetone are particularly pointed out. Thus, this process necessarily comprises the separation of the included solvent from the reaction mixture.

U.S. Pat. No. 4,182,920 is a further development of the previously described process and is also preferably aiming at the preparation of TAA. A novel feature particularly pointed out is that the whole feed mixture forms a single homogeneous phase and part of the isoamylene is fed into a second of a total of at least two reactors. As the solvent, acetone is particularly pointed out, and according to the Examples, it is present in an amount of from 60 to 75% by weight of the whole feed. This process is also performed with excess molar amounts of hydration water.

DE-A-35 12 518 describes the catalytic hydration of lower olefins, which are propene and n-butene according to the Examples. As the reaction parameters, conditions of from 120 to 180° C. under a pressure of from 40 to 200 bar on a strong ion exchanger in the presence of excess molar water amounts are selected. The excess process water is recirculated. Such conditions cause an increase of the differential pressure in the reactor and thus pressure surges, which eventually necessitates shut-down of the continuous reaction. Further, in the hydration of propene, hot spots in the catalyst bed were observed, which lead to by-products. To overcome these problems, the mentioned DE-A-35 12 518 describes the addition of a strong cationic surfactant, for which, however, the possibility of deactivation of the ion exchanger employed as catalyst is described in principle.

DE-A-38 01 275 describes the catalytic hydration of tertiary $C_4$ and $C_5$ olefins at moderately increased temperatures in the liquid phase. The reaction takes place in two or more serial tube reactors which contain an acidic ion exchanger. According to the Examples, the content of dimers in the product mixture is significantly decreased if from 0.2 to 5% by weight, based on the tertiary olefin to be hydrated, of tertiary $C_4$ or $C_5$ alcohol is added to the feed mixture. In this way, for example, a product mixture is obtained which has a maximum content of tertiary amyl alcohol of 26%.

The use of acidic ion exchanger loaded with an amphoteric element is described in EP-A-0 325 144. TAA is obtained in a fixed-bed reactor by the hydration of isoamylene, but the purity in the reaction mixture is only at up to 27% by weight. The proportion of dimers in the product mixture is clearly reduced in this way.

EP-A-0 325 143 also describes the preparation of TAA by the hydration of isoamylene on an acidic ion exchanger at a reaction temperature near the boiling point of isoamylene under the respectively set reaction pressure. This is effected without the addition of materials not involved in the reaction, especially without the addition of solvents. According to the Examples, a TAA content of up to 51% or a TAA yield of up to 46% is achieved for a synthesis in a fixed-bed reactor under normal pressure.

Can. J. Chem. Eng. 1993, 71, 821–823, describes the preparation of TAA in a fixed-bed reactor without the use of a solvent as a phase mediator. However, a maximum conversion of 12% is achieved.

All previously described processes share the disadvantage that the conversion of the process for the hydration of olefins is limited by the position of the chemical equilibrium. In all reactor types employed, the reaction space accommodates packings of solid catalyst particles which have a spherical or pellet-like design, for example, and are flowed around by the reactants. In the reactors having such a design, on the one hand, large pressure drops occur, and on the other hand, a homogeneous temperature distribution over the reactor cross-section does not occur. Another disadvantage is that there is no uniform concentration distribution over the reactor cross-section so that the yield of the desired final products is not optimum.

In contrast, the principle of reactive rectification has established as a method for achieving high conversions in thermodynamically limited material conversions. It is based on rectification running parallel with the reaction, whereby the higher boiling products come down in the column and are thus removed from the equilibrium. In addition, the heat dissipation in exothermic reactions can thus be controlled by the evaporation of the more volatile components, and the desired reaction temperature can be adjusted through the overall pressure.

The preparation of tertiary alcohols, especially tertiary amyl alcohol and tertiary butyl alcohol, by the hydration of the corresponding tertiary olefins by reactive rectification in the presence of an acidic ion exchanger is described in EP-A-0 415 310. In this case, the acidic ion exchanger is provided in a multitude of bags of a tissue band which is connected with a mesh wire structure of stain less steel for support, wherein the tissue band and the mesh wire structure are helically wound. The tissue band with the bags preferably consists of glass fibers. A drawback in this process is the fact that very different and in part little satisfactory results are obtained depending on the olefin employed and on the reaction conditions. For the conversion of isoamylene, for example, contents of only about 18 or 27% by weight of tertiary amyl alcohol are achieved in the bottoms of the column. Exact conversions or yields are not stated.

Ind. Eng. Chem. Res. 1997, 36, 3845–3853, also describes the synthesis of TAA with the catalytic packing described in EP-A-0 415 310 through a reactive rectification. Although high conversions, based on the isoamylene employed, are evidently achieved, the great disadvantage of poor reproducibility is present here too. A variability of ±20% is stated.

The above described wound bodies employed for the hydration of olefins by reactive rectification in EP-A-0 415

310 and Ind. Eng. Chem. Res. 1997, 36, 3845–3853, have some disadvantages: Due to the poor mixing and homogenizing properties of the wound bodies, there is no radial temperature and concentration equilibration over the column cross-section, on the one hand. On the other hand, due to the non-ordered flow form of the educts, products and by-products, a relatively large pressure drop over the packing occurs.

It has been the object of the present invention to provide a process which especially enables the preparation of tertiary alcohols by the hydration of the corresponding tertiary olefins with a high and reproducible conversion, with high purity of the alcohol in the reaction mixture, and a long service life of the catalyst employed.

SUMMARY OF THE INVENTION

The present invention relates to a process for the preparation of tertiary alcohols by reacting the corresponding tertiary olefins having the same number of carbon atoms with water in a heterogeneous reactive rectification in the presence of an acidic cation exchanger, characterized in that said process is performed using structured catalytic multi-purpose packings which have sections serving for material separation and sections serving as second functionality elements, wherein said sections serving as second functionality elements have a compartmental structure in which acidic cation exchangers are contained.

As compared to the known processes described above for the preparation of tertiary alcohols by reactive rectification, the process according to the invention is characterized in that the structured catalytic multi-purpose packings enable a clearly improved material exchange between gas/liquid in the sections serving for material separation and ensure a defined high distillation performance, so that very high yields and purities can be achieved. Thus, an exact calculation of fluid dynamics is also enabled.

BRIEF DESCRIPTION OF THE DRAWINGS

FIGS. 2a and b show a sectional front view of different embodiments of the second functionality element of the structured multi-purpose packing having closed chambers;

FIGS. 3a and b show a sectional side view of different embodiments of the second functionality element of the structured multi-purpose packing having closed chambers;

DETAILED DESCRIPTION OF INVENTION

Figure 1A:
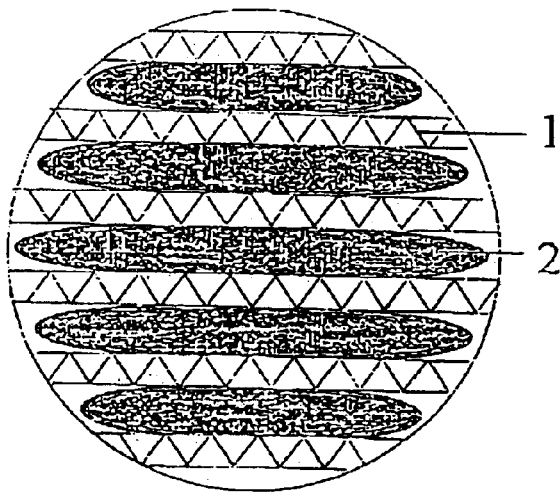
FIGS. 1a, b, and c show a top view of different embodiments of the structured multi-purpose packing.

The process according to the invention is particularly suitable for the preparation of tertiary $C_4$ to $C_8$ alcohols, preferably $C_5$, $C_6$ or $C_7$ alcohols, especially tertiary amyl alcohol (TAA), by reacting the corresponding tertiary olefins having the same number of carbon atoms, especially isoamylene, with water on an acidic ion exchanger.

In the process according to the invention, the tertiary olefins can be employed either in the form of distillation cuts containing the corresponding tertiary olefin, or else in an enriched or pure quality. Isoamylene (mixture of the isomers 2-methylbutene-1 and 2-methylbutene-2) can be employed, for example, in the form of a $C_5$ distillation cut which usually contains at least 5%, preferably at least 10%, by weight of isoamylene. In principle, such cuts contain, in addition to isoamylene, straight-chain $C_5$ olefins, certain amounts of the corresponding alkanes and some higher and lower hydrocarbon components. Preferably, an enriched isoamylene stream is used which usually contains about from 20 to 95% by weight of isoamylene. More preferably, an essentially pure isoamylene stream is employed which contains at least 95% by weight of isoamylene. Such an essentially pure isoamylene stream is obtained, for example, from the cleavage of tertiary amyl methyl ether (TAME).

In this reactive rectification, all known acidic cation exchangers obtainable by the polymerization or copolymerization of aromatic vinyl compounds followed by sulfonation can be employed as catalysts for the hydration of the tertiary olefins. Examples of aromatic vinyl compounds which may be employed for polymerization or copolymerization include: styrene, vinyl toluene, vinyl naphthalene, vinylethylbenzene, methylstyrene, vinylchlorobenzene and vinylxylene. The preparation method for these polymers or copolymers can be varied broadly. The homo- or copolymerization of the mentioned monomers can also be effected, for example, in the presence of polyvinyl compounds for cross-linking: Suitable polyvinyl compounds which may be used include divinylbenzene, divinyltoluene or divinylphenyl ether. The homo- or copolymers can be prepared in the presence or absence of solvents or dispersants using a wide variety of initiators, such as inorganic or organic peroxides or persulfates.

As acidic cation exchangers, sulfonated phenol-formaldehyde resins, sulfonated cumarone-indene condensation products, sulfonated polystyrenes or sulfonated styrene-divinylbenzene resins, above all, employed in their respective $H^+$ forms, have proven useful. Preferably, sulfonated styrene-divinylbenzene resins having a degree of cross-linking (divinylbenzene content) of from 2 to 65% by weight, preferably from 8 to 25% by weight, are employed. Such acidic cation exchangers are known to the skilled person and commercially available under many designations.

The process according to the invention is performed by loading the acidic cation exchangers with such an amount of total feed mixture that a liquid hourly space velocity (LHSV) of 0.05–1 | of feed mixture per liter of catalyst per hour, preferably 0.1–0.4 | of feed mixture per liter of catalyst per hour, is achieved.

By varying the amount of water employed in the preparation of tertiary alcohols in a reactive rectification by the process according to the invention, the product range of the conversion and the service life of the catalyst can be influenced. The amount of water employed can be superstoichiometric, equimolar or substoichiometric, based on the tertiary olefin employed. Preferably, an excess of water of from 10 to 90 mole percent, more preferably of from 30 to 70 mole percent, is employed. In particular, for the preparation of TAA from isoamylene and water, an excess of water of from 40 to 50 mole percent is used, based on the isoamylene employed.

When a lower amount of water is used, dimerization and in part also oligomerization of the tertiary olefin occur to a higher extent. The dimers and oligomers formed are very hydrophobic so as to impede the transport of water to the reaction centers. Since the water cannot react with the tertiary olefin unimpeded, low conversions result. In addition, dimers and oligomers deposit in the pores of the ion exchangers, can be hardly removed from the catalyst, for example, by rinsing, and thus cause an irreversible change of the initial morphology of the catalyst. Since part of the acidic sites of the catalyst are blocked in this way, the activity and thus the service life of the ion exchangers decrease.

On the other hand, the excess of water must not be too high either, since other-wise aqueous and organic phases form in the bottoms of the reactor of the reactive rectification, which results in the occurrence of delayed boiling. This leads to an unsteady operation of the reactor and prevents a good loading of the catalytic packing and thus a continuous preparation of the tertiary alcohols.

The reactive rectification according to the invention, for the preparation of tertiary alcohols yields the tertiary alcohol in a purity of from 50 to above 99% by weight, preferably from 70 to 95% by weight more preferably from 85 to 90%. If a further purification of the tertiary alcohol is desired, the reactive rectification may be followed by another distillation of the tertiary alcohol. Using azeotropic distillation with water separation, purities of above 99% by weight can be achieved. How to perform such a distillation is sufficiently known to the skilled person.

In the process according to the invention, structured multi-purpose packings can be employed, such as those described, for example, in U.S. Pat. No. 5,348,710, EP-A-0 428 265 (or the corresponding U.S. Pat. No. 5,073,236), EP-A-0 396 650 (or the corresponding U.S. Pat. No. 5,417, 938), EP-A-0 950 433 or DE-A-197 01 045, the disclosure of which with respect to the configuration of structured multi-purpose packings is incorporated herein by reference.

In such structured multi-purpose packings, the sections serving for material separation and the sections serving as second functionality elements are preferably provided alternately in layers. As represented, for example, in EP-A-0 950 433, DE-A-197 01 045 and EP 0 396 650 B2 (FIG. 1) and set forth in detail below, they can be provided as separate juxtaposed elements having different geometric designs. However, as represented in FIG. 5 of EP 0 396 650 B2, it is also possible to have a type of parallel folded layers each having a double coat, the cation exchanger being filled into the spaces between the double walls.

Multi-purpose packings structured in this way in accordance with the invention are commercially available, for example, as Katapak® from Gebrueder Sulzer AG or Multipak® from Montz GmbH, and are filled with the above described acidic cation exchanger.

Particularly useful are the structured multi-purpose packings as described in EP-A-0 950 433 or DE-A-197 01 045 and offered by Montz GmbH, containing material separation elements (1) and second functionality elements (2) provided in alternate layers, wherein the material separation elements have a profiled surface, and each of the second functionality elements has two or more closed chambers (3) provided on top of each other and filled with the acidic cation exchanger, a space being provided between any two of the chambers, which space is bridged by a section (6) conducting a liquid, the walls of the preferably pillow-shaped chambers of the second functionality elements being constituted of metal-wire cloth. The material separation elements have a profiled, preferably corrugated, surface. They are usually formed of metal sheets (7), preferably of black plate, stainless steel, hastelloy, copper or aluminum, or structured fabric sheets, for example, based on plastic materials, such as Teflon. The structure of such multi-purpose packings is explained in more detail by the FIGS. 1–5.

FIGS. 2a and b show a sectional front view of different embodiments of the second functionality element of the structured multi-purpose packing having closed chambers.

FIGS. 3a and b show a sectional side view of different embodiments of the second functionality element of the structured multi-purpose packing having closed chambers.

Figure 4A:
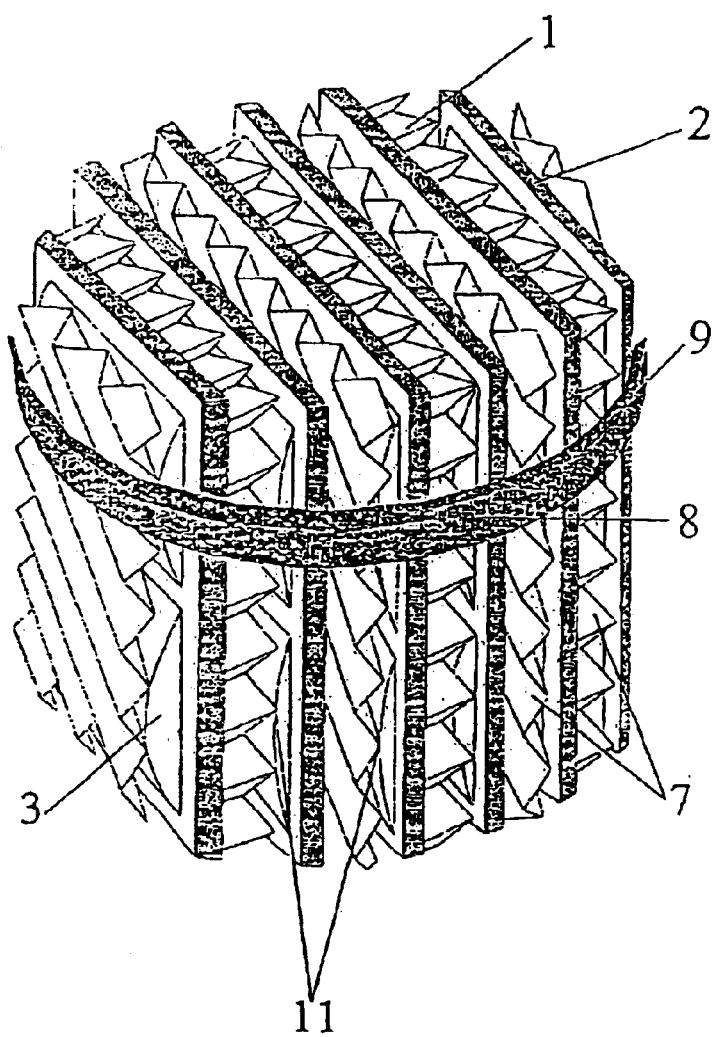
FIGS. 4a and b a perspective view of different embodiments of the structured multi-purpose packing having second functionality elements and material separation elements.

FIGS. 4a and b show a perspective view of different embodiments of the structured multi-purpose packing having second functionality elements and material separation elements.

Figure 1B:
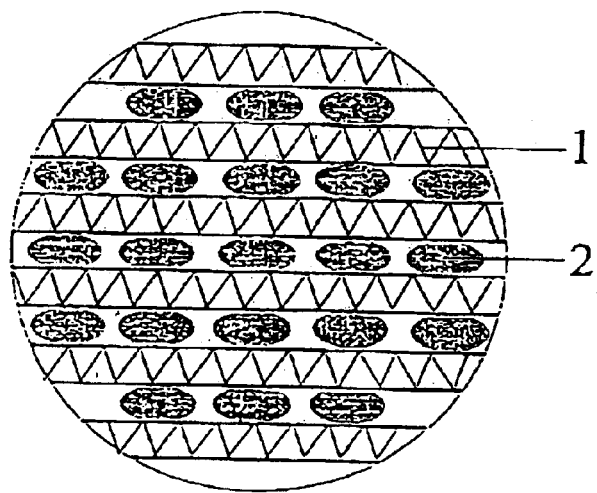
Figure 1C:
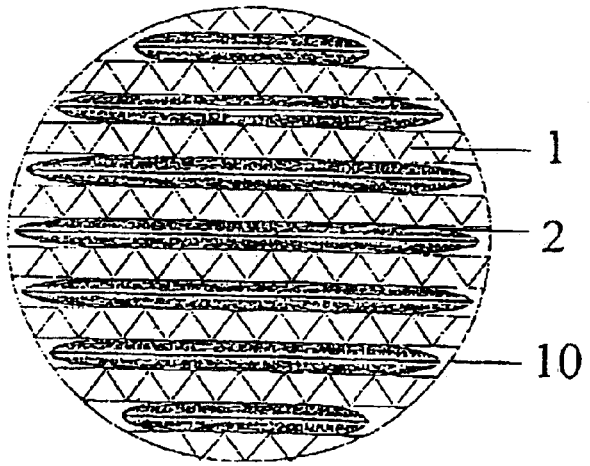
Figure 4B:
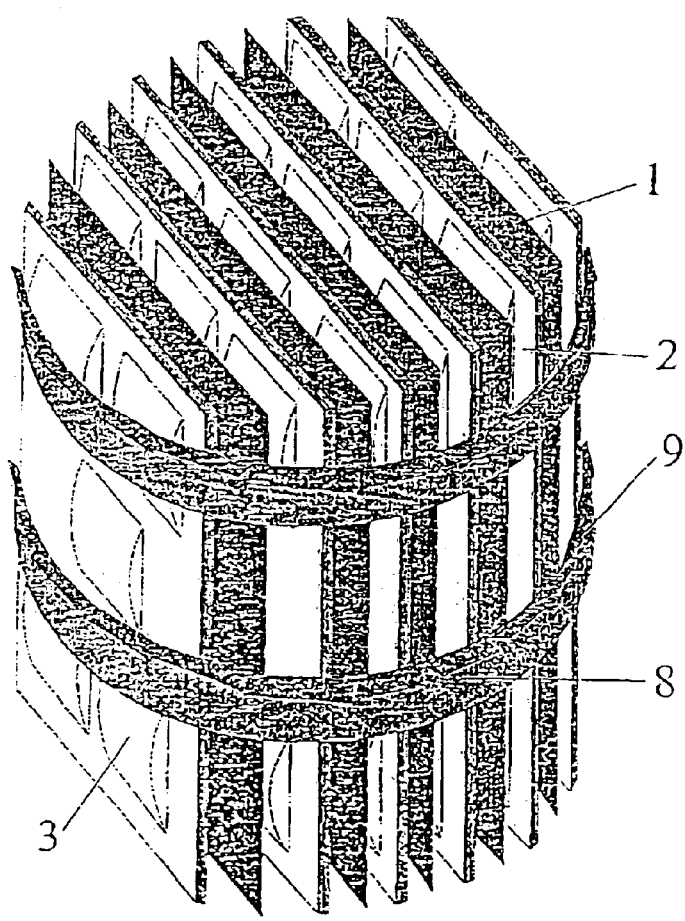

As shown in FIGS. 4a and 4b, the material separation elements (1) and second functionality elements (2) represented in FIGS. 1a, b and c are provided in alternate layers. The number and volume of the second functionality elements and the number of the material separation elements can be varied depending on the reaction system considered, which is illustratively shown in the different embodiments in FIGS. 1a, b and c. Therefore, the residence times and effective surface areas in the second functionality elements as well as the contact areas in the material separation elements can be tailored in view of the material system considered. When mounted, the second functionality elements can be reinforced by fluid-permeable stabilizing metal sheets (10) as in FIG. 1c, which is not necessarily required for functional reasons, however, cf. FIGS. 1a and b.

In FIGS. 2a and b, a front view of different embodiments of the second functionality element is seen. In all embodiments, the completely closed and sufficiently small chambers (3) provided on top of each other which are filled, for example, with catalytic, adsorbing or biologically active material can be seen. The walls of the chambers are fluid-permeable but impermeable to the packing material. As shown in FIG. 2b, a plurality of chambers (3) can be arranged in a horizontal layer and can be alternately displaced in the next lower layer. It is also possible to provide only one closed chamber in every horizontal layer, as in FIG. 2a. The chambers (3) and conducting sections (6) together form a vertical sheet layer (2).

FIGS. 3a and b show side views of a second functionality element having closed chambers (3). The chambers are formed by tightly joining the upper and lower sides of the lateral walls 4a and 4b of the second functionality elements both at the edges (5) and in the chamber interspaces (6), so that the chambers are tightly closed with respect to the packing material. This joining if effected, for example, by welding. It is useful to leave a little free space between the second functionality elements and the edges of the packing in order to facilitate flowing around the second functionality elements.

FIGS. 4a and b show a perspective view of an element of the structured multipurpose packing. The arrangement of the different functional parts in alternating layers can be seen. The material separation elements (1) which exclusively serve the function of material separation consist of structured fabric sheets or metal sheets (7) with different profiles. It is advantageous if the orientation of the channels of the fabric sheets changes alternately. A wide variety of designs of structured fabric sheets can be employed, the most suitable being selected to provide a purposeful optimization with respect to the intended application of the multi-purpose packing. At their points of contact (11), the different functional units can be tightly joined, but this may also be omitted in favor of a higher flexibility. A skirt (8) with lobe-like protrusions (9), as usual with structured packings, tightly encloses the functional elements and in addition stabilizes the multi-purpose packing within the column.

The packing element shown is designated for a multi-purpose column having a circular cross-section, but the realization of the multi-purpose packing is basically possible for all cross-sections.

Figure 5A:
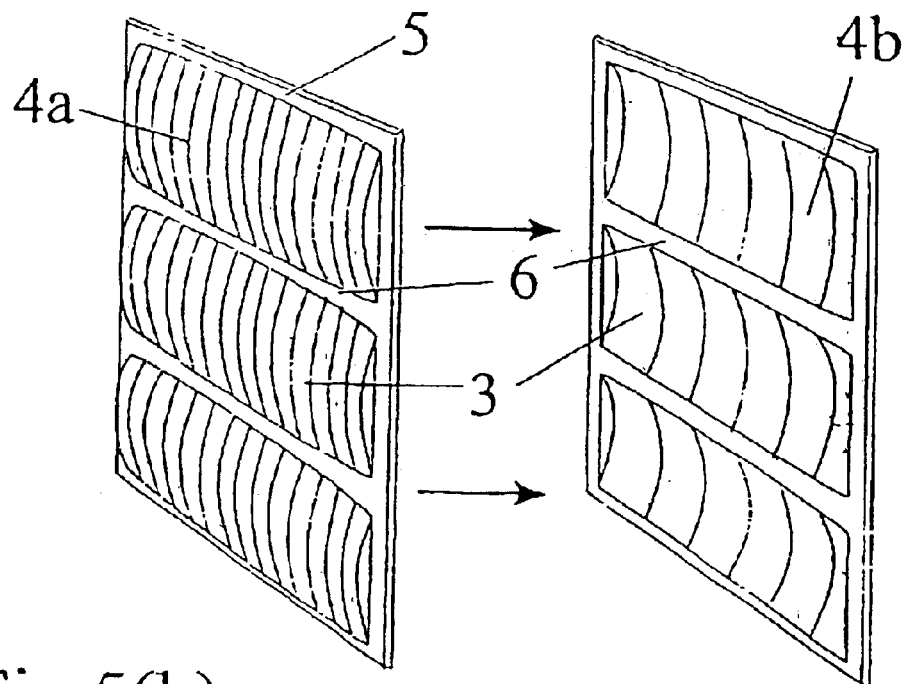
FIGS. 5a and b show a front view of different embodiments of the second functionality element of the structured multi-purpose packing with disassembled walls.
Figure 5B:
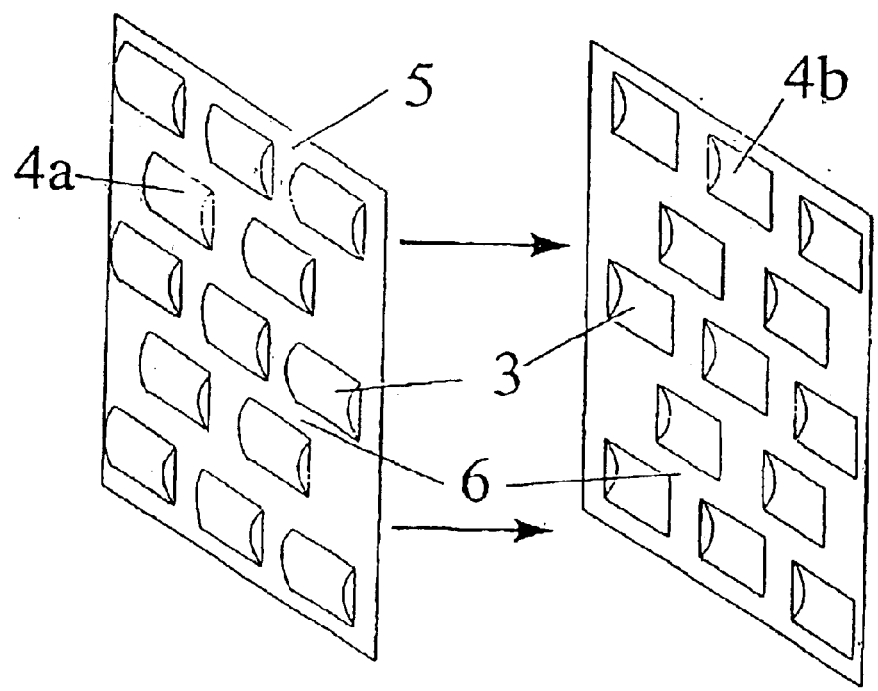

FIGS. 5a and b show different embodiments of the configuration of a second functionality element. Two preformed fabric sheets (4a and 4b) are joined together. The generated chambers (3) are filled prior to being closed. A complete filling of the chambers is not necessary. The filling amount is also variable to provide a purposeful optimization with respect to the intended use.

Figure 6:
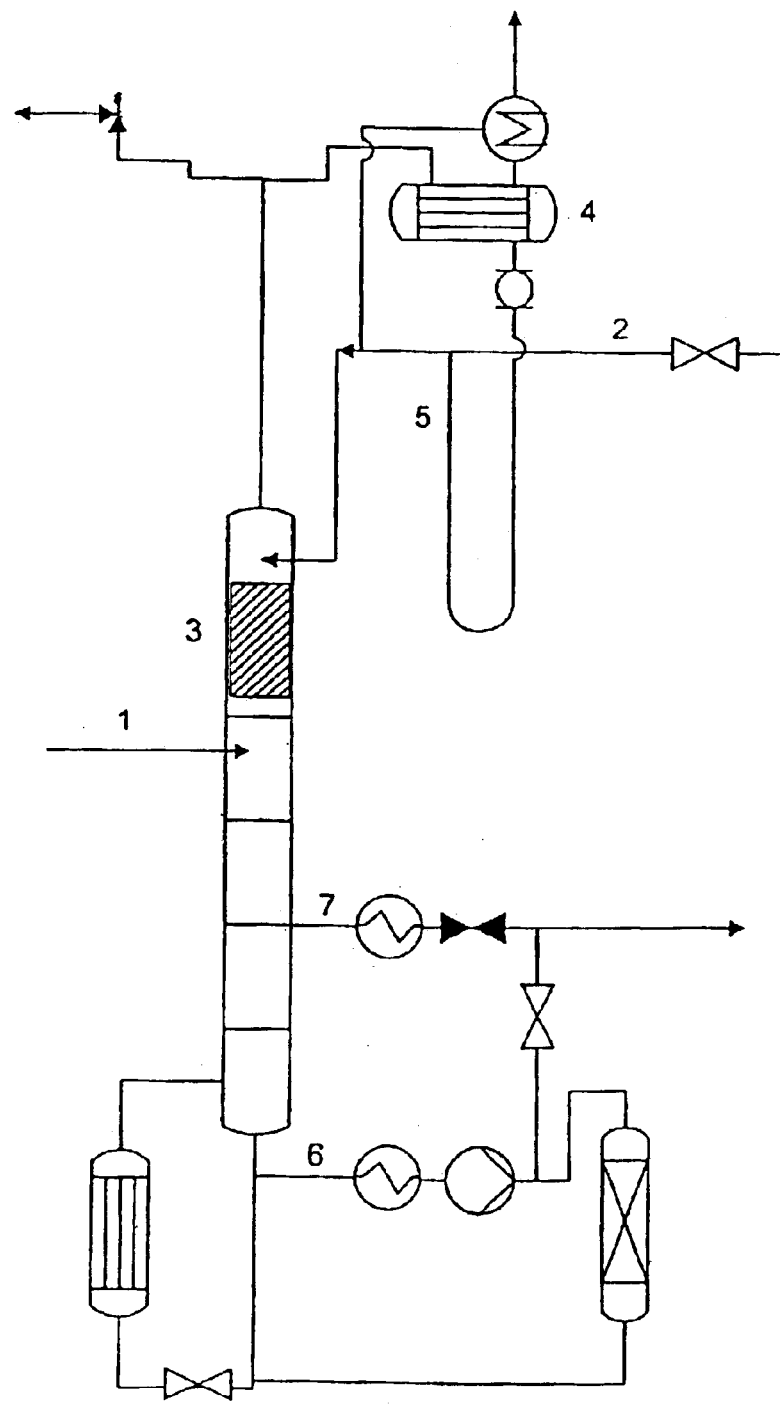
FIG. 6 shows the structure of a reactor for the preparation of tertiary alcohols in a reactive rectification using the structural multi-purpose packing.

FIG. 6 shows the structure of a reactor for the preparation of tertiary alcohols in a reactive rectification using a structured multi-purpose packing according to the invention. The feeding of the tertiary olefin stream is effected through feed line (R1) below the structured multi-purpose packing. The feeding of the water is effected through feed line (R2) above the structured multi-purpose packing. Thus, the tertiary olefin and the water flow in counter-current through the structured multi-purpose packing (R3) over the ion exchanger contained therein, filled in chambers. At the head of the column, unreacted tertiary olefin is condensed in an azeotrope with water (in the case of TAA preparation from 98% by weight of isoamylene and 2% by weight of water) (R4) and recirculated into the column together with fresh water above the catalytic packing (R5). The tertiary alcohol prepared and excess water go into the bottoms of the reactor; from there (R6) are optionally through a side stream (R7), they are removed and, in the case where a further purification is desired, fed to a distillation column for azeotropic distillation.

EXAMPLES

Examples 1 and 2

Preparation of Tertiary Amyl Alcohol (TAA)

The preparation of TAA is effected by reacting isoamylene and water in a continuously operated reactive rectification in the reactor shown in FIG. 6. The diameter of the column is 55 mm. The diameter of the packing is 213 mm. The setting of the quantity recycled is 25 kg/h at an infinite recycle ratio. The temperature in the reactor is about 60° C. at the level of the multi-purpose packing and between 110 and 125° C. in the bottoms for a total pressure of 2.2 bar in the column.

The multifunctional packing Multipak® of Montz GmbH in which the walls of the chambers of the second functionality elements are made of steel serves as the structured multi-purpose packing. This multi-purpose packing is filled with about 4 kg (corresponding to 5.5 liters) of a styrene-divinylbenzene resin containing acidic sulfur groups (commercial product Lewatit® K2631 of Bayer AG).

An isoamylene stream obtained by the cleavage of tertiary amyl methyl ether and having a purity of above 99% by weight of isoamylene serves as the feed stream.

The remaining experimental conditions and the results of the reactive rectification are shown in Table 1.

TABLE 1

|  | B1 | B2 | B3 | B4 |
| --- | --- | --- | --- | --- |
| isoamylene feed stream [g/h] | 300 | 600 | 800 | 1200 |
| water feed [g/h] | 75 | 144 | 224 | 312 |
| ratio of water/isoamylene in the feed stream [g/g] | 0.25 | 0.24 | 0.28 | 0.26 |
| TAA production [g/h] | 293 | 604 | 668 | 887 |
| TAA content in the bottoms [%] | 81.4 | 87.7 | 69.5 | 55.6 |
| TAA conversion, based on isoamylene feed stream [%] | 77.8 | 80.1 | 67.1 | 58.2 |

What is claimed is:

1. A process for the preparation of tertiary alcohols comprising reacting tertiary olefins having the same number of carbon atoms as the tertiary alcohols to be prepared with water in a heterogeneous reactive rectification in the presence of an acidic cation exchanger, the process being performed in the presence of structured catalytic multi-purpose packings which have sections serving for material separation and sections serving as second functionality elements, wherein said sections serving as second functionality elements have a compartmental structure in which said acidic cation exchanger is contained.

2. The process of claim 1, wherein the tertiary alcohols to be prepared are $C_4$ to $C_8$ alcohols.

3. The process of claim 2, wherein the alcohols to be prepared are $C_5$ to $C_7$ alcohols.

4. The process of claim 3, wherein the alcohol to be prepared is tertiary amyl alcohol and the tertiary olefin is isoamylene.

5. The process of claim 1 or 2, wherein the acidic cation exchanger is selected from the group consisting of a sulfonated phenol-formaldehyde resin, a sulfonated cumarone-indene condensation product, sulfonated polystyrene or a sulfonated styrene-divinylbenzene resin in their respect H* forms.

6. The process of claim 5, wherein the sulfonated styrene-divinylbenzene resin has a degree of cross-linking (divinylbenzene content) of from 2 to 65% by weight.

7. The process of claim 6, wherein the degree of cross-linking is from 8 to 25% by weight.

8. The process of claim 1, wherein the acidic cation exchanger is loaded with such an amount of total feed mixture of tertiary olefin and water that a liquid hourly space velocity of 0.05–1 | of feed mixture per liter of catalyst per hour, is achieved.

9. The process of claim 8, wherein the liquid hourly space velocity is 0.1–0.4 | of feed mixture per liter of catalyst per hour.

10. The process of claim 1, wherein the amount of water employed is superstoichiometric, equimolar or substoichiometric, based on the tertiary olefin.

11. The process of claim 10, where an excess of water of from 10 to 90 mole percent is employed.

12. The process of claim 11, wherein the excess of water is from 30 to 70 mole percent.

13. The process of claim 4, wherein an excess of water of from 40 to 50 mole percent, based on the isoamylene is used for the preparation of the tertiary amyl alcohol.

14. The process of claim 1, wherein the structured multi-purpose packings contain material separation elements and second functionality elements provided in alternate layers, the material separation elements have a profiled surface, and each of the second functionality elements having two or more closed chambers provided on top of each other and filled with the acidic cation exchanger, a space being provided between any two of the chambers, which space is bridged by a section conducting a liquid, the walls of the second functionality elements being constituted of metal-wire cloth.

* * * * *

UNITED STATES PATENT AND TRADEMARK OFFICE
CERTIFICATE OF CORRECTION

PATENT NO. : 6,951,967 B2
APPLICATION NO. : 10/365497
DATED : October 4, 2005
INVENTOR(S) : Axel Gohrt et al.

It is certified that error appears in the above-identified patent and that said Letters Patent is hereby corrected as shown below:

Title page, item [73], "Assignee: EC Erdolchemie GmbH, Cologne (DE); Bayer AG, Leverkusen (DE)" should read --Assignee: BP Koln GmbH, Cologne (DE) and Bayer AG, Leverkusen (DE)--.

Signed and Sealed this

Seventh Day of November, 2006

JON W. DUDAS
*Director of the United States Patent and Trademark Office*